United States Patent
Tsaur et al.

(10) Patent No.: US 11,160,347 B1
(45) Date of Patent: Nov. 2, 2021

(54) USE AND METHOD OF GAS SUPPLY DEVICE FOR LIGHTENING HAIR COLOR

(71) Applicant: TO2M CORPORATION, Hsinchu (TW)

(72) Inventors: Garry Tsaur, Rowland Heights, CA (US); Ting-Hua Wang, Rowland Heights, CA (US)

(73) Assignee: TO2M CORPORATION, Hsinchu (TW)

(*) Notice: Subject to any disclaimer, the term of this patent is extended or adjusted under 35 U.S.C. 154(b) by 0 days.

(21) Appl. No.: 16/865,798

(22) Filed: May 4, 2020

(51) Int. Cl.
| | | |
|---|---|---|
| *A45D 19/18* | (2006.01) | |
| *A45D 19/00* | (2006.01) | |
| *A61K 8/22* | (2006.01) | |
| *A61K 8/362* | (2006.01) | |
| *A61K 8/365* | (2006.01) | |
| *A61Q 5/08* | (2006.01) | |
| *A61K 8/19* | (2006.01) | |
| *A45D 7/00* | (2006.01) | |

(52) U.S. Cl.
CPC ............ *A45D 19/00* (2013.01); *A45D 19/18* (2013.01); *A61K 8/19* (2013.01); *A61K 8/22* (2013.01); *A61K 8/362* (2013.01); *A61K 8/365* (2013.01); *A61Q 5/08* (2013.01); *A45D 2007/001* (2013.01)

(58) Field of Classification Search
CPC ... A61Q 5/08; A61K 8/19; A61K 8/42; A61K 8/66; A61K 2800/87; A61K 8/365; A61K 8/362; A61K 8/22; A45D 2007/001; A45D 19/00
USPC .......................................................... 132/270
See application file for complete search history.

(56) References Cited

U.S. PATENT DOCUMENTS

| | | | | |
|---|---|---|---|---|
| 5,058,609 | A | * 10/1991 | Sandoz | A45D 19/018 132/270 |
| 2010/0126522 | A1 | * 5/2010 | Fujinuma | A61Q 5/10 132/208 |
| 2010/0126523 | A1 | * 5/2010 | Fujinuma | B05B 11/048 132/221 |
| 2012/0028874 | A1 | * 2/2012 | Fernandez Prieto | C11D 11/0088 510/375 |
| 2015/0096583 | A1 | * 4/2015 | Cordoba Ramos | A45D 24/02 132/200 |

* cited by examiner

*Primary Examiner* — Eisa B Elhilo
(74) *Attorney, Agent, or Firm* — WPAT, PC

(57) ABSTRACT

The present invention provides a gas supply device for lightening hair color, including a separating layer and a functional unit wrapped in the separating layer, wherein the functional unit includes a metal peroxide, an activator and a catalyst, the gas supply device further wraps a composition that generates carbon dioxide, nitric oxide, and/or hydrogen. The present invention discloses a use and method of a gas supply device for lightening hair color, including supplying oxygen to the scalp and the hair, and further reacting to generate active oxygen. The present invention further discloses a method for eliminating a dye on the hair by using the gas supply device.

25 Claims, 7 Drawing Sheets

USE AND METHOD OF GAS SUPPLY DEVICE FOR LIGHTENING HAIR COLOR

TECHNICAL FIELD

The present invention relates to a gas supply device for lightening hair color and a use thereof.

BACKGROUND

Modern people care much about hair color. Nowadays, more and more young people will dye their hair to change the original hair color. It is regarded as fashionable and popular. And for the older people, their appearance and self-confidence will be affected by whitened hair. They will also seek ways to dye hair to address the problem of white hair.

The original color of the hair is mainly related to the melanin produced in the scalp hair follicles. The melanin can be divided into eumelanin and pheomelanin, which are produced from tyrosine through a series of reactions under the action of tyrosinase. For Asians, their scalp hair follicles mainly produce eumelanin, so their hair color appears black; while for westerners with red-brown hair, their scalp hair follicles mainly produce pheomelanin, which makes their hair color reddish brown. As we are aging, hydrogen peroxide will gradually accumulate in our hair follicles, which will inhibit the activity of tyrosinase involved in the formation of melanin, resulting in a decrease in the production of melanin in the hair follicles, which in turn causes the newly generated hair to appear white, that is the so called white hair.

The hair color can be effectively changed through hair dyeing. However, the current dyes used in hair dyeing are in liquid or colloidal state, which makes them easily touch the scalp and cause discomfort. Also, the steps to apply them are lengthy and complicated, and the cost is relatively high. On the other hand, hair dyeing agents often involve the use of chemicals that can remove, replace, or hide pigments in natural hair, and the use of these chemicals can cause a range of adverse effects, including skin irritation and allergies, hair breakage, hair quality deterioration and skin discoloration and other problems. According to the research data provided by the International Agency for Research on Cancer (IARC), some dyes and chemicals used in the process of hair dyeing are considered to increase the risk of cell mutation and carcinogenesis.

Therefore, there is an urgent need in the art to find a hair dyeing method that is easy to operate, has low cost, and is free of undesirable side effects, to reduce the risk of damage to the human body by chemical dyes.

In addition, after the hair is dyed, the dyeing results are often unsatisfactory. In this case, one must wait for the hair to grow back to the original hair color, so it takes a long time and one has to endure the unsatisfactory hair color until new hair grows back. If you want to modify the hair dyeing results in a short time, you need to bleach or re-dye the hair. This requires a large additional cost, and it is easy to cause additional damage to the hair and skin.

Therefore, another major problem urgently to be solved in the art is how to change the hair dyeing results in a way that has less side effects on the human body to remove the dye and make the hair return to the original hair color with less cost.

SUMMARY

In view of the shortcomings and deficiencies of the prior art, an objective of the present invention is to provide a method of lightening hair color which is easy to operate, has low cost and does not use liquid or colloidal chemical dyes, thereby preventing the chemical dyes from damaging hair and skin while changing hair color.

In order to achieve the above objective of the invention, the present invention provides a gas supply device for lightening hair color. The gas supply device comprises a separating layer and a functional unit wrapped in the separating layer, wherein the functional unit comprises a metal peroxide, an activator and a catalyst.

The separating layer may be a single layer or a composite layer. The separating layer may be made of a breathable material or a non-breathable material; the material of the two sides of the separating layer may be different.

The metal peroxide in the functional unit comprises calcium peroxide, magnesium peroxide, sodium peroxide, or potassium peroxide.

The activator in the functional unit is an amide compound selected from the group consisting of tetraacetylethylenediamine (TAED), sodium nonanoyloxybenzene sulfonate (NOBS), tetraethylglycoluril, penta-acetyl glucopyranose, N-acetylphthaloyl imide, 1-acetylethyl benzoate, triacetyl ethanolamine and nonylacetylphenyl sulfonate.

The catalyst in the functional unit is catalase.

The gas supply device is a device for the head.

The gas supply device is a device for the trunk or limbs.

In order to achieve the aforesaid objective of the invention, the gas supply device provided by the present invention further wraps a carbon dioxide generating composition and/or a nitric oxide generating composition so as to enhance the efficiency of hair color lightening.

The carbon dioxide generating composition comprises a solid acid and solid sodium bicarbonate or a metal carbonate; the solid acid is lactic acid and/or citric acid; and the metal carbonate includes magnesium carbonate, calcium carbonate, sodium carbonate, or potassium carbonate.

The nitric oxide generating composition comprises a metal unit and a nitric acid wrapping unit; wherein, the nitric acid wrapping unit seals nitric acid therein, the nitric acid can be released by breaking the nitric acid wrapping unit, and the nitric acid is dilute nitric acid; wherein the metal unit is selected from the group consisting of sodium, magnesium, aluminum, zinc, iron, tin, lead, copper, silver, and combinations thereof; wherein, the nitric acid wrapping unit is a metal composite membrane with high gas barrier and water barrier property, an inner layer of the metal composite membrane is a polymer film, and an outer layer of the metal composite membrane is a metal film.

The nitric oxide generating composition further comprises a deoxidizer, a superabsorbent polymer, an activator, or a catalyst; the deoxidizer comprises an iron-based deoxidizer, a sulfite-based deoxidizer, or a hydrogenation catalyst deoxidizer.

The polymer film is selected from the group consisting of polyethylene, polypropylene, polyethylene terephthalate (PET), aluminized PET film, polysilazane coated PET, cast polypropylene film (CPP), aluminized CPP film, aluminum oxide composite PET/CPP, copolyester plastics and combinations thereof.

The metal film is made of a material selected from the group consisting of sodium, magnesium, aluminum, zinc, iron, tin, lead, copper, silver and combinations thereof.

In order to achieve the aforesaid objective of the present invention, the gas supply device provided by the present invention further wraps a hydrogen generating composition.

The hydrogen generating composition comprises (1) a metal hydroxide or a metal peroxide and an aluminum powder, (2) a hydride or (3) a combination of the two.

The metal hydroxide in the hydrogen-generating composition comprises calcium hydroxide, magnesium hydroxide, sodium hydroxide, or potassium hydroxide; the metal peroxide comprises calcium peroxide, magnesium peroxide, sodium peroxide, or potassium peroxide; and the hydride comprises hydrides that can react with water to generate hydrogen.

The gas supply device as described above, wherein the weight ratio of the functional unit to the carbon dioxide generating composition is 1:100-100:1; wherein the weight ratio of the functional unit to the nitric oxide generating composition is 1:100-100:1; wherein, the weight ratio of the functional unit to the hydrogen generating composition is 1:100-100:1.

The gas supply device as described above, wherein the weight ratio of the functional unit to the carbon dioxide generating composition is 1:10-10:1; wherein the weight ratio of the functional unit to the nitric oxide generating composition is 1:10-10:1; wherein, the weight ratio of the functional unit to the hydrogen generating composition is 1:10-10:1.

The gas supply device as described above may further comprise at least one duct connected to the separating layer.

The gas supply device as described above may be used for a head-worn device or a hairdressing apparatus; wherein the head-worn device comprises a head shield, a safety helmet, a hat, a shower cap or a swimming cap; and the hairdressing apparatus includes an air blower, a hair dryer or a perm machine.

In order to achieve the aforesaid objective of the present invention, the present invention provides a use of the above gas supply device for lightening hair color, which comprises providing gas to the scalp and the hair, wherein the gas is oxygen and can further react to generate active oxygen which is capable of lightening hair color and promoting hair growth; wherein the gas may further comprise carbon dioxide, nitric oxide and/or hydrogen.

A method for lightening a hair color using the above gas supply device, comprising the following steps:

step 1: placing the gas supply device in a head-worn device;

step 2: wearing the head-worn device at a position where the hair is to be lightened for 1-4 hours;

step 3: repeating this procedure 4-5 times, with an interval of 1-3 days therebetween.

Previous studies have revealed that hydrogen can be used to change white hair into black hair. Therefore, for users with white hair, hydrogen can be applied to the scalp and hair before step 1 to change the hair to black before the gas supply device provided by the present invention is applied to supply active oxygen to the scalp and hair to lighten the color of black hair, thereby achieving the effect of changing hair color.

Among others, the method can spray a little water on the gas supply device before use to speed up the reaction.

Another objective of the present invention is to provide a method for eliminating a hair dye that is easy to operate, has low cost, and is relatively free of side effects.

To achieve the above objective of the present invention, the present invention provides a use of the gas supply device as described above for eliminating a dye on the hair, wherein the eliminating the dye on the hair is to change the hair color back to the original hair color.

The method for lightening hair color provided by the present invention does not irritate hair and skin, nor induces allergic reactions, and its cost is lower than that of the chemical dyes used in the past. Also, this method is relatively simple to operate and can effectively change hair color.

The present invention also discloses a head-worn device or a hairdressing apparatus that can be used to lighten hair color. The head-worn device can put the scalp or hair in an atmosphere of oxygen or other gases, and it is close to the skin, so that the oxygen or other gases is easily absorbed by the hair follicle. Also, it has the advantage of being portable. The hairdressing apparatus can allow the user's hair and scalp to be in an environment of oxygen and other gases during hairdressing to simultaneously perform hairdressing and hair color lightening. The gas environment also has the effect of promoting the growth of hair follicles.

Figure 1:
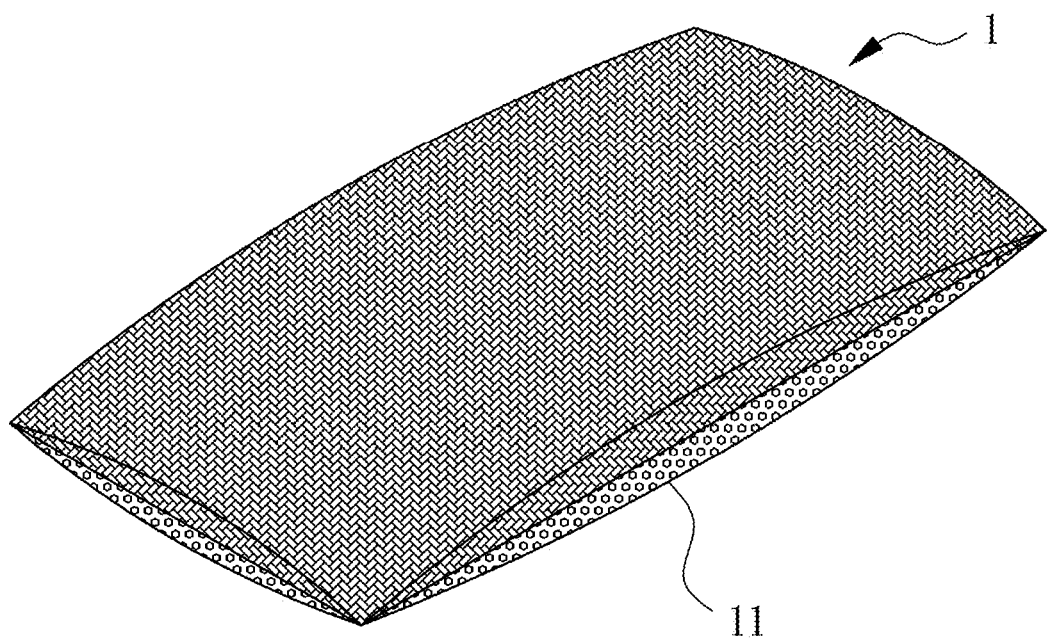
FIG. 1 is a schematic diagram of the gas supply device.

The patent or application file contains at least one drawing executed in color. Copies of this patent or patent application publication with color drawings will be provided by the Office upon request and payment of the necessary fee.

1 Gas supply device
11 Separating layer
111 Breathable structure
12 Functional unit
13 Carbon dioxide generating composition
14 Metal unit
141 Nitric acid packing unit
15 Hydrogen generating composition
16 Duct

DETAILED DESCRIPTION

Unless otherwise defined, all technical and scientific terms described in the specification of the present invention have the meanings that can be commonly understood by those skilled in the art.

The term "original hair color" in this specification refers to the color of hair grown out of healthy, undamaged and unaged hair follicles of adult individuals. The original hair color may be different due to the difference in the ability of pigment production of healthy hair follicles among individuals.

The term "lighten hair color" in the specification refers to changing the hair color to a lighter color than the original one, for example, changing black hair into brown hair. The color change differs depending on the original hair color or the dyeing procedure.

Figure 2:
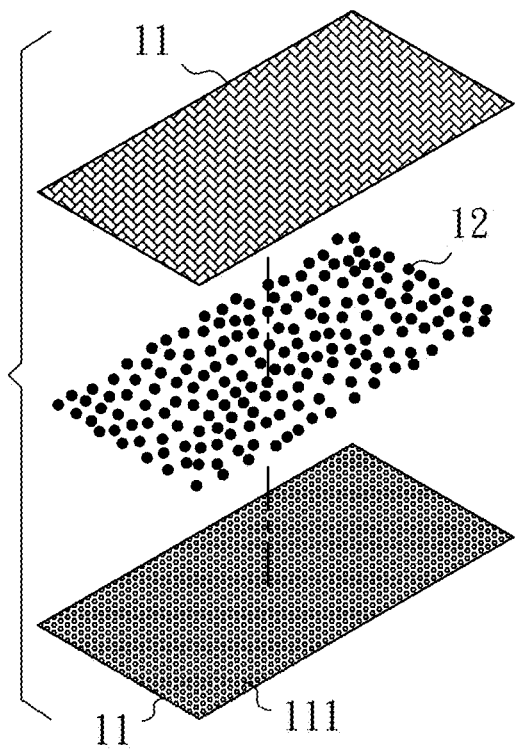
FIG. 2 is an exploded view of the gas supply device.
Figure 3:
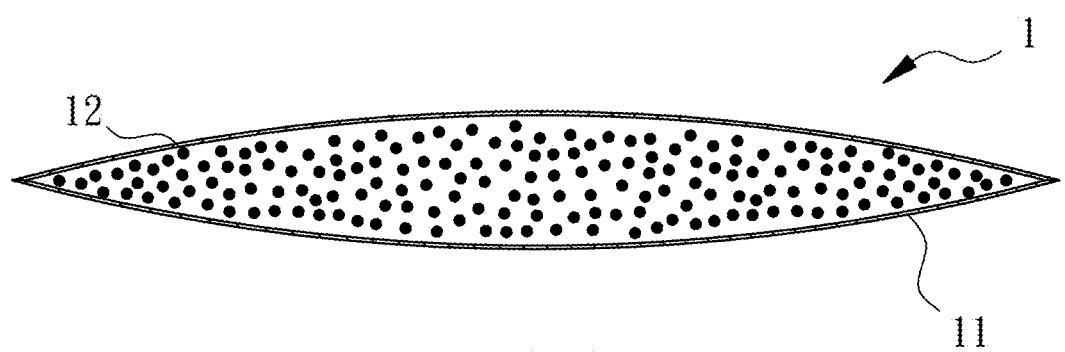
FIG. 3 is a cross-sectional view of the gas supply device.

The present invention provides a gas supply device 1 for lightening hair color. As shown in FIGS. 1-3, the gas supply device 1 includes a separating layer 11 and a functional unit 12 wrapped in the separating layer 11. The separating layer 11 may be a single layer or a composite layer; the separating layer 11 may be made of a breathable material or a non-breathable material. In a preferred embodiment of the present invention, the side of the separating layer 11 close to the user is a breathable structure 111 to allow gas to enter and exit. The materials of the two sides of the separating layer 11 may be different. The functional unit 12 includes a metal peroxide, an activator, and a catalyst. The metal peroxide includes calcium peroxide, magnesium peroxide, sodium peroxide, or potassium peroxide.

Among others, the activator in the functional unit 12 is an acyl compound selected from the group consisting of tetraacetylethylenediamine (TAED), sodium nonanoyloxybenzene sulfonate (NOBS), tetraethylglycoluril, penta-acetyl glucopyranose, N-acetylphthaloyl imide, 1-acetylethyl benzoate, triacetyl ethanolamine and nonylacetylphenyl sulfonate. Among others, the catalyst in the functional unit 12 is catalase.

The present invention provides a use for lightening hair color by supplying active oxygen to the scalp and hair using the gas supply device 1, wherein the active oxygen has the effect of lightening hair color and can promote the growth of hair. The functional unit 12 can interact with the water vapor in the environment or the water vapor emitted by the human body to generate active oxygen, or it can react with a pre-prepared aqueous liquid. The reaction equation is as follows:

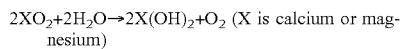
$2XO_2 + 2H_2O \rightarrow 2X(OH)_2 + O_2$ (X is calcium or magnesium)

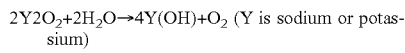
$2Y_2O_2 + 2H_2O \rightarrow 4Y(OH) + O_2$ (Y is sodium or potassium)

The intermediate product of the above reaction, hydrogen peroxide ($H_2O_2$), like a weak acid, dissociates into anion of hydrogen peroxide in an alkaline medium:

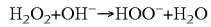
$H_2O_2 + OH^- \rightarrow HOO^- + H_2O$

Hydrogen peroxide anion is a nucleophilic reagent that can make hydrogen peroxide form free radicals:

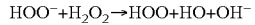
$HOO^- + H_2O_2 \rightarrow HOO + HO + OH^-$

They both have high activity, which can oxidize and decompose the pigments in the hair to produce an effect similar to bleaching to lighten hair color.

The gas supply device 1 is a device for the head.

The gas supply device 1 is a device for the trunk or limbs.

The present invention further applies the above principle to dyed hair, and finds that it has the effect of eliminating the dye. Therefore, a method for eliminating a dye on the hair is proposed, which uses the gas supply device 1 as described above to supply active oxygen to the scalp and hair. Among others, the eliminating a dye on the hair comprises changing the hair color back to the original hair color.

The present invention is exemplified and clarified by the following examples. It is to be understood that the examples described are only to illustrate the technical ideas and features of the present invention, and to enable those skilled in the art to understand and implement the contents of the present invention, but not to limit the scope of the present invention. That is, any changes or modifications made in accordance with the spirit disclosed by the present invention should still be covered by the scope of this patent.

Example 1: Experiment of Hair Color Lightening Using Gas 100 g of calcium peroxide ($CaO_2$) as the solid oxygen source, 0.5 g of catalase (CAT) as the catalyst, and 10 g of tetraacetylethylenediamine (TAED) as the activator were made into the functional unit 12 of the gas supply device 1 as described above, placed in a head shield, as shown in FIG. 4, and further tested for its effect of lightening hair color.

Figure 11:
FIG. 11 is a picture showing a head shield installed with the gas supply device.

Several subjects with black hair were recruited. The subjects were allowed to wear the head shield for 1-4 hours each time, 4-5 times in total, with an interval of 1-3 days therebetween. How the subject looked like when wearing the head shield is shown in FIG. 11. The changes in scalp condition and hair color were observed and recorded.

Figure 12:
FIG. 12 is a photograph showing the hair color of a subject in Example 1 before use.
Figure 13:
FIG. 13 is a photograph showing the hair color of the subject in Example 1 after use.

As shown in FIG. 12, the subject's hair color was black (PANTONE Black C) before use. After continuous use of the head shield for 4-5 times, the subject's hair color changed from black to reddish brown, as shown in FIG. 13. This hair color has a PANTONE color code number 1675C (red-brown). The hair color tended to be lightened significantly, and the color change was significant.

In addition, when the subject wore the head shield, there was no discomfort, and after removing the head shield, the scalp did not have redness or allergies, showing that the method and device provided by the present invention will not irritate the scalp Irritating or cause other undesirable side effects.

Example 2: Experiment of Hair Color Lightening Using Gas—in Combination with Carbon Dioxide Generating Composition In this example, the above-described gas supply device 1 further wraps a carbon dioxide generating composition 13 that includes a solid acid and solid sodium bicarbonate or metal carbonate.

The solid acid in the carbon dioxide generating composition 13 is lactic acid and/or citric acid; wherein the metal carbonate includes magnesium carbonate, calcium carbonate, sodium carbonate or potassium carbonate; wherein the weight ratio of the solid acid to the solid sodium bicarbonate or metal carbonate is 1:100-100:1, and preferably 1:10-10:1.

The steps of this example are as follows:

1. 10 g of magnesium peroxide ($MgO_2$) as the solid oxygen source, 0.5 g of catalase (CAT) as the catalyst, 0.05 g of tetraacetylethylenediamine (TAED) as the activator were made into a functional unit 12, and 0.7 g of citric acid and 0.5 g of sodium bicarbonate were made into a carbon dioxide generating composition 13.

Figure 4:
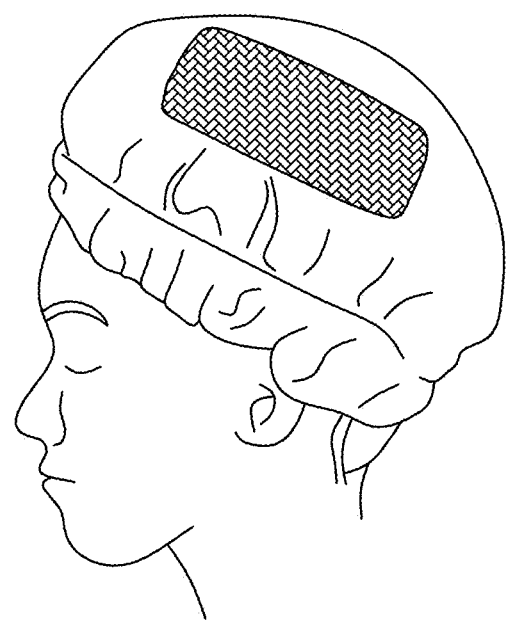
FIG. 4 is a schematic view of a head shield including a gas supply device.
Figure 5:
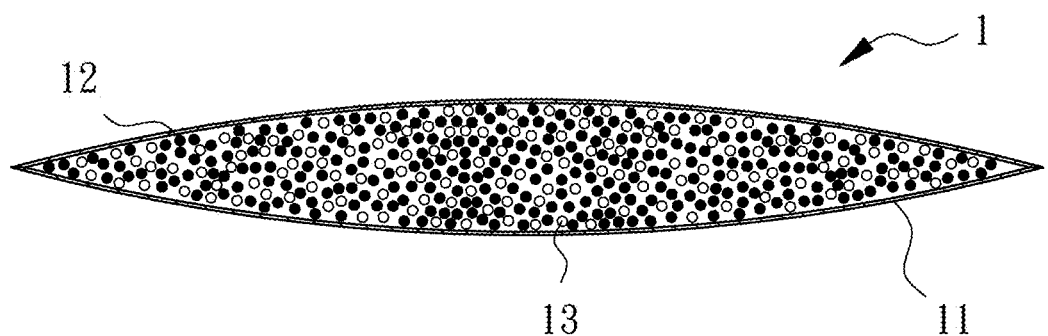
FIG. 5 is a cross-sectional view of the gas supply device of Example 2.

2. The above-mentioned functional unit 12 and the carbon dioxide generating composition 13 were made into the gas supply device 1 according to the present invention, as shown in FIG. 11, and the gas supply device was placed in a head shield, as shown in FIG. 4.

3. Users wore the head shield for 1-4 hours a day, 4-5 times in total, with an interval of 1-3 days therebetween.

The carbon dioxide generating composition 13 of this example can generate carbon dioxide by interacting with the water vapor in the environment or the water vapor emitted by the human body, and the reaction equation is as follows:

$$3NaHCO_3 + C_3H_4(OH)(COOH)_3 \rightarrow C_3H_4(OH)(COONa)_3 + 3H_2O + 3CO_2$$

Studies have shown that carbon dioxide has the function of expanding microvessels, so that it can accelerate the gas (oxygen) exchange rate. Therefore, this embodiment uses carbon dioxide to work together to accelerate the reaction and obtain better hair color lightening effect.

Example 3: Experiment of Hair Color Lightening Using Gas—in Combination with Nitric Oxide Generating Composition In this example, the above-described gas supply device 1 further wraps a nitric oxide generating composition. The nitric oxide generating composition includes a metal unit 14 and a nitric acid wrapping unit 141; wherein, the nitric acid wrapping unit 141 seals nitric acid therein, the nitric acid can be released by destroying the nitric acid wrapping unit 141, and the nitric acid is dilute nitric acid; wherein, the metal unit 14 is selected from the group consisting of sodium, magnesium, aluminum, zinc, iron, tin, lead, copper, silver and combinations thereof; wherein, the nitric acid wrapping unit 141 is a metal composite film with high gas- and water-barrier property, the inner layer of the metal composite film is a polymer film, and the outer layer of the metal composite film is a metal film; wherein, the polymer film is selected from the group consisting of polyethylene, polypropylene, polyethylene terephthalate (PET), aluminized PET film, polysilazane coated PET, cast polypropylene film (CPP), aluminized CPP film, aluminum oxide composite PET/CPP, copolyester plastics and combinations thereof; wherein, the metal film is made of a material selected from the group consisting of sodium, magnesium, aluminum, zinc, iron, tin, lead, copper, silver and combinations thereof.

The nitric oxide generating composition may further include a deoxidizer, a super absorbent polymer, an activator, or a catalyst; the deoxidizer includes an iron-based deoxidizer, a sulfite-based deoxidizer, or a hydrogenation catalyst-type deoxidizer.

In an embodiment of the present invention, when needed, the nitric acid wrapping unit 141 can be destroyed to release dilute nitric acid. When the dilute nitric acid contacts the metal unit 14, they can react to form nitric oxide. The reaction is shown below.

$$3X + 8HNO_3 \rightarrow 3X(NO_3)_2 + 2NO\uparrow + 4H_2O$$

$$Y + 4HNO_3 \rightarrow Y(NO_3)_3 + NO\uparrow + 2H_2O$$

$$3Z + 4HNO_3 \uparrow 3ZNO_3 + NO\uparrow + 2H_2O$$

where, X is magnesium, aluminum, zinc, iron, tin, lead, or copper, Y is aluminum, iron, or copper, Z is sodium or silver; wherein, the nitric acid is dilute nitric acid; wherein, the weight ratio of nitric acid to water is 1:3-1:20, preferably 1:4-1:6, and most preferably 1:5.

The steps of this example are as follows:

1. 50 g of potassium peroxide ($K_2O_2$) as the solid oxygen source, 1 g of catalase (CAT) as the catalyst, and 0.3 g of sodium nonanoyloxybenzene sulfonate (NOBS) were made into the functional unit 12.

2. The nitric acid coating unit 141 and 5 g of sodium metal were made into a nitric oxide generating composition.

Figure 6:
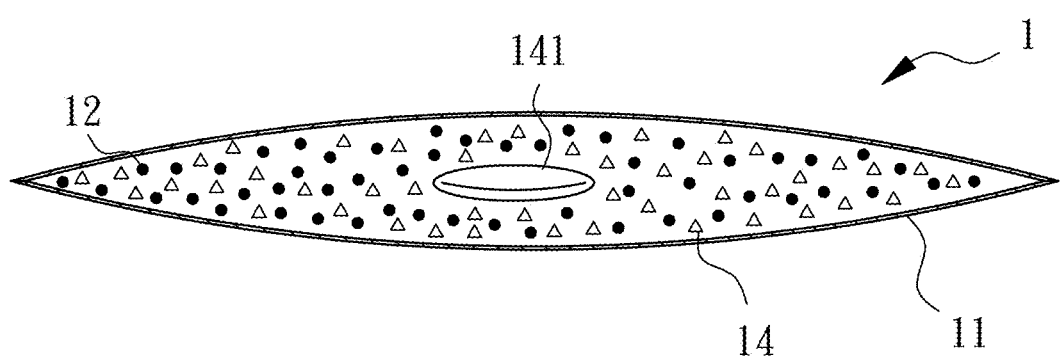
FIG. 6 is a cross-sectional view of the gas supply device of Example 3.
Figure 7:
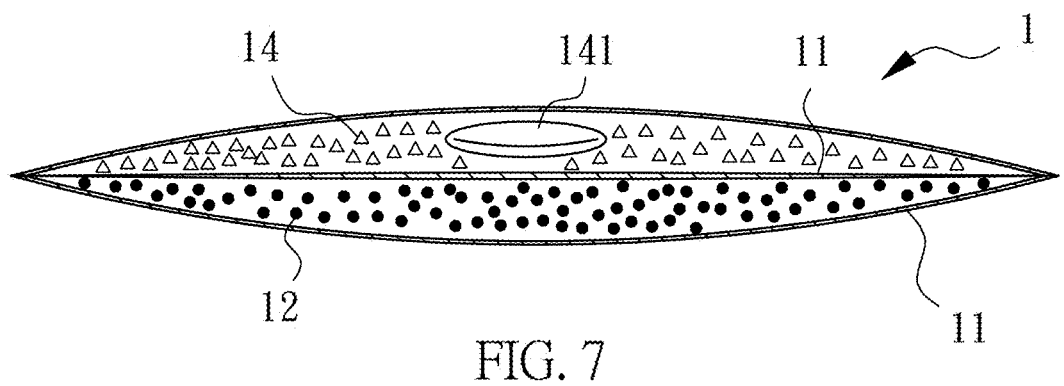
FIG. 7 is a cross-sectional view of another gas supply device of Example 3.

3. The functional unit 12 and the nitric oxide generating composition described above were made into the gas supply device 1 according to the present invention, as shown in FIG. 6, and placed in a head shield, as shown in FIG. 4. The gas supply device 1 can also be divided into different sections through the separating layer 11 to separate the compositions therein, as shown in FIG. 7.

4. The user wore the head shield for 1-4 hours a day, 4-5 times in total, with an interval of 1-3 days therebetween.

Studies have shown that nitric oxide has the functions of expanding microvessels and accelerating blood flow, so that it can accelerate the gas (oxygen) exchange rate. Therefore, this example uses nitric oxide to work together to accelerate the reaction and obtain better hair color lightening effect.

Example 4: Experiment of Hair Color Lightening Using Gas—in Combination with Hydrogen This example further uses the aforementioned gas supply device 1 in combination with a hydrogen generating composition. The hydrogen generating composition 15 includes (1) s metal hydroxide or metal peroxide and an aluminum powder, (2) a hydride or (3) a combination of the above two.

The metal hydroxide in the hydrogen generating composition 15 includes calcium hydroxide, magnesium hydroxide, sodium hydroxide or potassium hydroxide; the metal peroxide includes calcium peroxide, magnesium peroxide, sodium peroxide or potassium peroxide; the hydride includes hydrides that can react with water to generate hydrogen.

Previous studies have shown that hydrogen has the effect of improving white hair. This is realized by eliminating hydrogen peroxide in the hair and hair follicles using hydrogen. The reaction formula is as follows:

$$H_2 + H_2O_2 \rightarrow 2H_2O$$

In this example, when the hydrogen generating composition 15 includes a metal hydroxide and an aluminum powder, the metal hydroxide can react with the aluminum powder to generate hydrogen, with the reaction formulas as shown below:

$$2Al + 2H_2O + X(OH)_2 \rightarrow X(AiO2)_2 + 3H_2 \text{ (X is calcium or magnesium)}$$

$$2Al + 2H_2O + 2Y(OH) \rightarrow 2YAlO_2 + 3H_2 \text{ (Y is sodium or potassium)}$$

When the hydrogen generating composition 15 includes a metal peroxide and an aluminum powder, the metal peroxide can react with water vapor in the environment to generate a metal hydroxide, and can simultaneously generate oxygen, as shown in the following reaction formula:

$$2XO_2 + 2H_2O \rightarrow 2X(OH)_2 + O_2 \text{ (X is calcium or magnesium)}$$

$$2Y2O_2 + 2H_2O \rightarrow 4Y(OH) + O_2 \text{ (Y is sodium or potassium)}$$

The generated metal hydroxide can then generate hydrogen through reaction between the metal hydroxide and the aluminum powder as shown in the above reaction formula.

The steps of this embodiment are as follows:

1. 2 g of sodium peroxide ($Na_2O_2$) as the solid oxygen source, 0.05 g of catalase (CAT) as the catalyst and 0.04 g of penta-acetyl glucopyranose were weighed and made into the functional unit 12 of the gas supply device 1 as described above, and 1 g of sodium peroxide, 1 g of sodium hydroxide, 10 g of aluminum powder and an appropriate amount of oxalic acid were made into the hydrogen generating composition 15.

Figure 8:
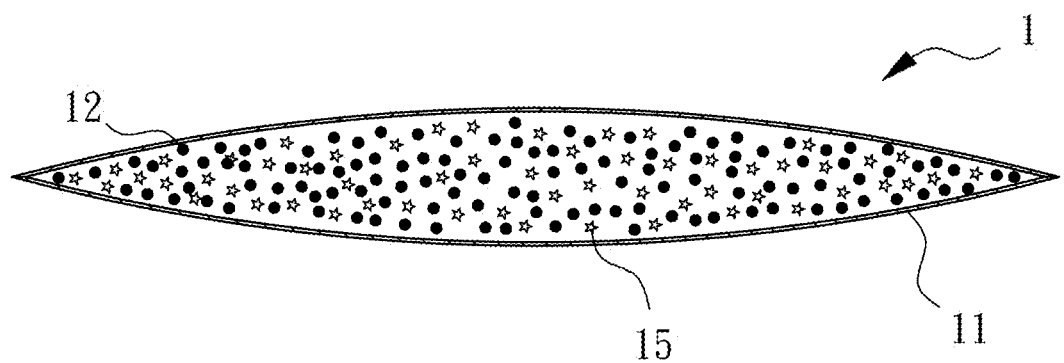
FIG. 8 is a cross-sectional view of the gas supply device of Example 4.

2. The above-mentioned functional unit 12 and hydrogen-generating composition 15 were made into the gas supply device 1 according to the present invention, as shown in FIG. 8, and placed in a head shield, as shown in FIG. 4.

3. The user wore the head shield for 1-4 hours a day, 4-5 times in total, with an interval of 1-3 days therebetween.

Figure 14:
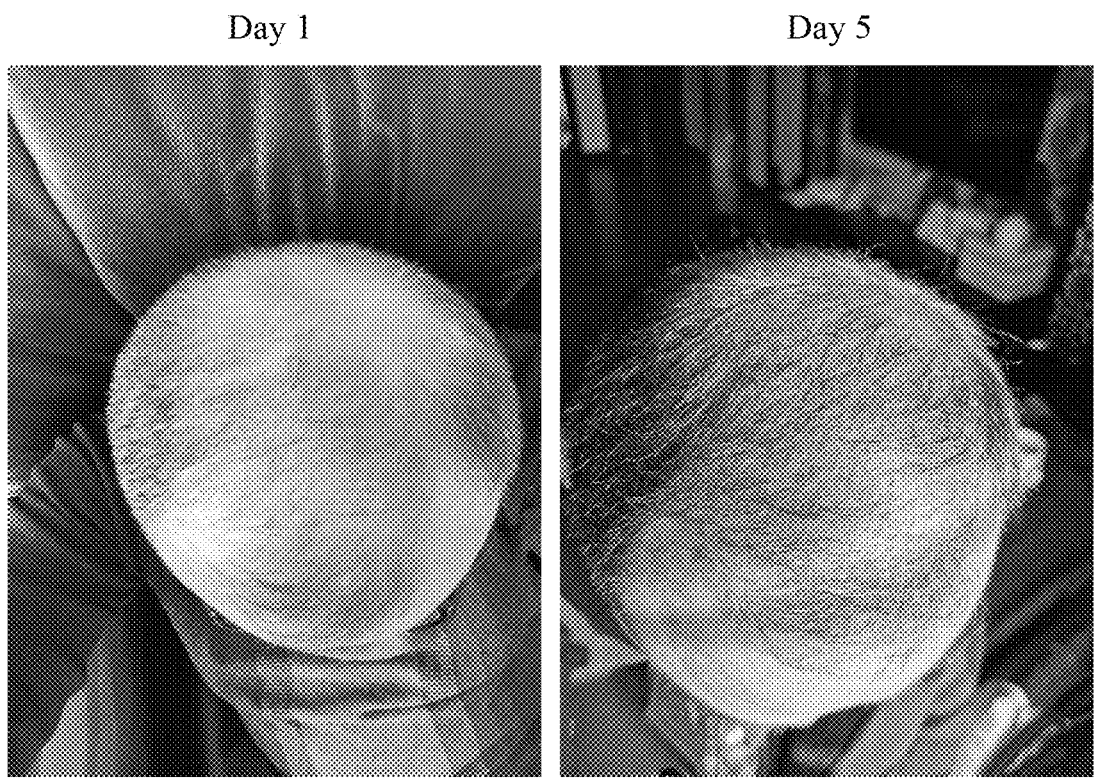
FIG. 14 is a photograph showing the hair color of a subject of Example 4 before use (Day 1) and after use (Day 5).

The experimental results of one of the subjects in this example are shown in FIG. 14. The subject's hair color was white before using the head shield (Day 1). After using the head shield for 5 consecutive days (Day 5), the subject's hair color changed from white to PANTONE color code number 160C (brown), which is due to the effect of hydrogen of improving white hair, and the effect of the formula of the present invention of lightening hair color. As a result, the hair color tended to become obviously lightened. In another embodiment of the present invention, the hydrogen generating composition 15 and the functional unit 12 can be made into different gas supply devices 1. First, white hair is changed into black hair using the hydrogen supply device, and then the resultant black hair is lightened using the gas supply device 1 comprising the functional unit 12 of the present invention, so as to achieve the effect of improving the white hair while dyeing it.

Example 5. Experiment of Hair Dye Elimination Using Gas 50 g of calcium peroxide ($CaO_2$) as the solid oxygen source, 0.5 g of catalase (CAT) as the catalyst, and 10 g of triacetylethanolamine as the activator were made into the functional unit 12 of the gas supply device 1 as described above and placed in a head shield, as shown in FIG. 4.

This example is used for users with dyed hair of various colors. The users were allowed to wear the head shield for 1-4 hours a day, 4-5 times in total, with an interval of 1-3 days therebetween. This can remove the dye on the user's hair, so that the hair color changes back to the original hair color. Therefore, this example has the effect of eliminating the dye on the hair.

Example 6. Gas Supply Device Comprising Duct

Figure 9:
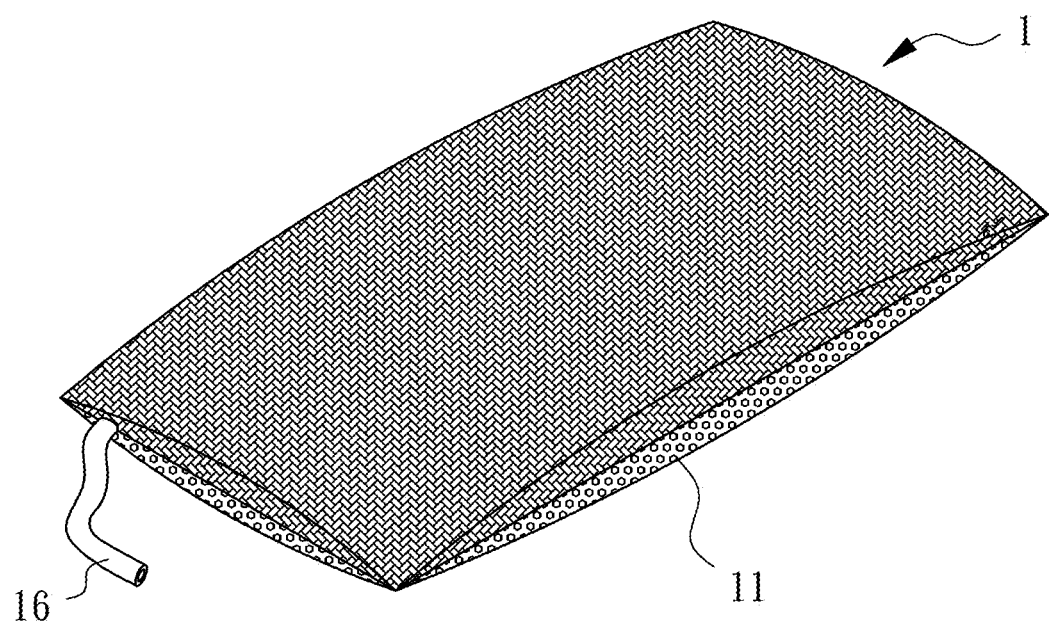
FIG. 9 is a schematic diagram of the gas supply device with a duct.

The gas supply device 1 provided by the present invention may further comprise at least one duct 16. As shown in FIG. 9, the duct 16 is connected to the separating layer 11 and can be used to discharge the gas generated by the gas supply device 1.

Example 7. Hairdressing Apparatus Comprising Gas Supply Device

Figure 10:
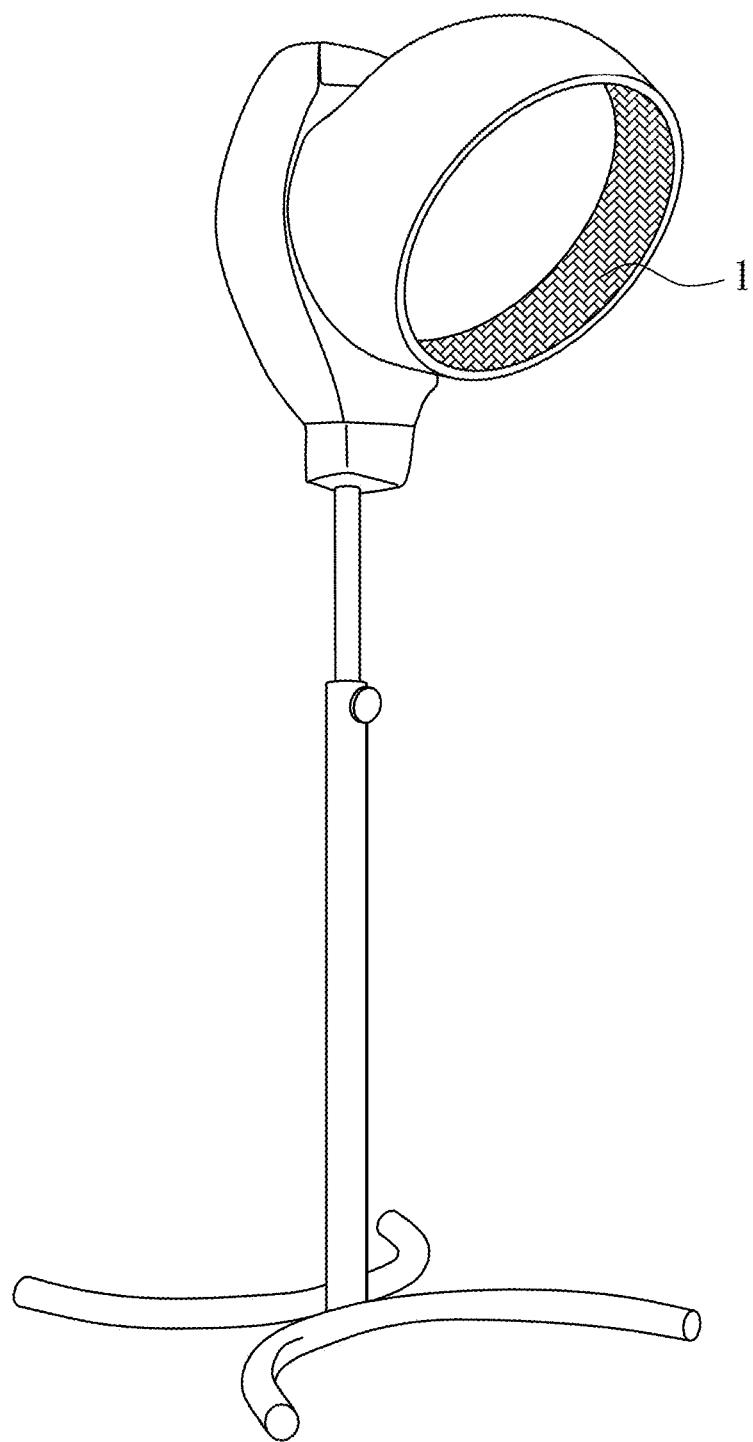
FIG. 10 is a schematic diagram of the gas supply device installed in a hairdressing apparatus.

The gas supply device 1 provided by the present invention can be used with a hairdressing apparatus. As shown in FIG. 10, the gas supply device 1 described above is installed on a hairdressing apparatus to supply active oxygen to the scalp and hair during the hairdressing process. As a result, the pigments in the hair are oxidized and decomposed to produce an effect similar to hair dyeing to lighten hair color.

In order to find a proper ratio between the reactants, 0.01-100 g of the reactants of the above examples were taken to test for their gas generation efficiency. It was found that the weight ratio of the functional unit 12 to the carbon dioxide generating composition 13 is 1:100-100:1, and most preferably is 1:10-10:1; the weight ratio of the functional unit 12 to the nitric oxide generating composition is 1:100-100:1, and most preferably 1:10-10:1; and the weight ratio of the functional unit 12 to the hydrogen generating composition 15 is 1:100-100:1, and most preferably 1:10-10:1.

The gas supply device 1 of the present invention can be used in a head-worn device or a hairdressing apparatus; wherein the head-worn device includes a head shield, a safety helmet, a hat, a shower cap or a swimming cap; wherein the hairdressing apparatus includes an air blower, a hair dryer or a perm machine.

The present invention provides a gas supply device as described above for lightening hair color, which comprises providing gas to the scalp and hair, wherein the gas is oxygen, and can further react to generate active oxygen, which has the effect of promoting hair color lightening and can promote the growth of hair; wherein the gas may further include carbon dioxide, nitric oxide and/or hydrogen.

The present invention provides a method for lightening hair color using the gas supply device as described above, which includes the following steps:

step 1: placing the gas supply device in a head-worn device;

step 2: wearing the head-worn device at a position where the hair is to be lightened for 1-4 hours;

step 3: repeating this procedure 4-5 times, with an interval of 1-3 days therebetween.

For uses with white hair, hydrogen gas can be applied to the scalp and hair before step 1 to dye the hair black first, and then the gas supply device provided by the present invention can be applied to supply active oxygen to the scalp and hair to lighten the black hair, thereby achieving the effect of changing hair color.

In this method, a little water can be sprayed on the gas supply device before use to speed up the reaction.

The present invention further provides a use of the gas supply device as described above for eliminating a dye on the hair, wherein the eliminating the dye on the hair changes the hair color back to the original hair color.

In summary, the present invention provides a new method of lightening hair color, which can also be regarded as a hair dyeing method to promote the color change of hair. Compared with traditional methods, the method provided by the present invention has the advantages of low cost, easy operation and easy maintenance.

The method provided by the present invention can apply the gas supply device of the above examples to supply active oxygen and other gases to the scalp and hair, so as to achieve the effect of lightening hair color, wherein the other gases include carbon dioxide, nitric oxide and/or hydrogen.

The method provided by the present invention can be further applied to hair dyeing. The hair dyeing is not limited to changing the color of hair on the head, but can also be used to change the color hair of the trunk and limbs. Compared with traditional methods for dyeing hair, the present invention does not use chemical dyes, so that it does not have the risk of cell mutation or carcinogenesis, and can even achieve hair dyeing without stimulating the scalp or skin.

In addition, some studies have pointed out that when the scalp is hypoxic, the hair follicles will enter a state of programmed cell death, resulting in damage and atrophy of the hair follicles, which in turn leads to abnormal hair loss, reduced hair volume, and the possibility of baldness. It can be seen that the gas supply device 1 including the functional unit 12 of the present invention also contributes to the growth of hair.

In addition, the method for lightening hair color provided by the present invention can be used together with a head-worn device or a hairdressing apparatus. The head-wearing device provided by the present invention has the advantage of being portable and allows the user to dye hair at any time. The hairdressing apparatus provided by the present invention allows the user to dye hair at the same time with hairdressing, thereby saving time advantageously.

The above detailed descriptions are specific descriptions of possible embodiments of the present invention, but these embodiments are not intended to limit the scope of the present invention. Any equivalent implementation or change without departing from the technical spirit of the present invention should be covered in scope of this patent.

The above-mentioned multiple functions are in full compliance with the statutory patent requirements for novelty and progress. This patent application is hereby filed in accordance with the law, approval of this patent application by your office is deeply appreciated.

What is claimed is:

1. A gas supply device for lightening hair color, comprising a separating layer and a functional unit wrapped in the separating layer, wherein the functional unit comprises a metal peroxide, an activator and a catalyst.

2. The gas supply device according to claim 1, wherein the separating layer is a single layer or a composite layer.

3. The gas supply device according to claim 1, wherein the metal peroxide in the functional unit comprises calcium peroxide, magnesium peroxide, sodium peroxide, or potassium peroxide.

4. The gas supply device according to claim 1, wherein the activator in the functional unit is an amide compound selected from the group consisting of tetraacetylethylenediamine (TAED), sodium nonanoyloxybenzene sulfonate (NOBS), tetraethylglycoluril, penta-acetyl glucopyranose, N-acetylphthaloyl imide, 1-acetylethyl benzoate, triacetyl ethanolamine and nonylacetylphenyl sulfonate.

5. The gas supply device according to claim 1, wherein the catalyst in the functional unit is catalase.

6. The gas supply device according to claim 1, wherein the gas supply device is a device for the head.

7. The gas supply device according to claim 1, wherein the gas supply device is a device for the trunk or limbs.

8. The gas supply device according to claim 1, wherein the gas supply device further wraps a carbon dioxide generating composition and/or a nitric oxide generating composition.

9. The gas supply device according to claim 8, wherein the carbon dioxide generating composition comprises a solid acid and solid sodium bicarbonate or a metal carbonate.

10. The gas supply device according to claim 9, wherein the solid acid in the carbon dioxide generating composition is lactic acid and/or citric acid.

11. The gas supply device according to claim 9, wherein the metal carbonate in the carbon dioxide generating composition includes magnesium carbonate, calcium carbonate, sodium carbonate, or potassium carbonate.

12. The gas supply device according to claim 8, wherein the nitric oxide generating composition comprises a metal unit and a nitric acid wrapping unit; wherein, the nitric acid wrapping unit seals nitric acid in it, the nitric acid can be released by breaking the nitric acid wrapping unit, and the nitric acid is dilute nitric acid; wherein the metal unit is selected from the group consisting of sodium, magnesium, aluminum, zinc, iron, tin, lead, copper, silver, and combinations thereof; wherein, the nitric acid wrapping unit is a metal composite membrane with high gas barrier and water barrier property, an inner layer of the metal composite membrane is a polymer film, and an outer layer of the metal composite membrane is a metal film.

13. The gas supply device according to claim 12, wherein the nitric oxide generating composition further comprises a deoxidizer, a superabsorbent polymer, an activator, or a catalyst; the deoxidizer comprises an iron-based deoxidizer, a sulfite-based deoxidizer, or a hydrogenation catalyst deoxidizer.

14. The gas supply device according to claim 12, wherein the polymer film is selected from the group consisting of polyethylene, polypropylene, polyethylene terephthalate (PET), aluminized PET film, polysilazane coated PET, cast polypropylene film (CPP), aluminized CPP film, aluminum oxide composite PET/CPP, copolyester plastics and combinations thereof.

15. The gas supply device according to claim 12, wherein the metal film is made of a material selected from the group consisting of sodium, magnesium, aluminum, zinc, iron, tin, lead, copper, silver and combinations thereof.

16. The gas supply device according to claim 1, wherein the gas supply device further wraps a hydrogen generating composition.

17. The gas supply device according to claim 16, wherein the hydrogen generating composition comprises
    (1) a metal hydroxide or a metal peroxide and an aluminum powder,
    (2) a hydride or
    (3) a combination of the two.

18. The gas supply device according to claim 17, wherein the metal hydroxide in the hydrogen-generating composition comprises calcium hydroxide, magnesium hydroxide, sodium hydroxide, or potassium hydroxide; the metal peroxide comprises calcium peroxide, magnesium peroxide, sodium peroxide, or potassium peroxide; and the hydride comprises a hydride that can react with water to generate hydrogen.

19. The gas supply device according to claim 1, wherein the gas supply device further comprises at least one duct connected to the separating layer.

20. The gas supply device according to claim 1, wherein the gas supply device is used for a head-worn device or a hairdressing apparatus.

21. The gas supply device according to claim 20, wherein the head-worn device comprises a head shield, a safety helmet, a hat, a shower cap or a swimming cap.

22. The gas supply device according to claim 20, wherein the hairdressing apparatus includes an air blower, a hair dryer or a perm machine.

23. A method for lightening a hair color using the gas supply device according to claim 1, comprising the following steps:
    step 1: placing the gas supply device in a head-worn device;
    step 2: wearing the head-worn device at a position where the hair is to be lightened for 1-4 hours;
    step 3: repeating this procedure 4-5 times, with an interval of 1-3 days therebetween.

24. The method according to claim 23, wherein a hydrogen gas can be applied to the scalp and the hair before step 1.

25. The method according to claim 23, wherein a water is sprayed on the gas supply device before use.

* * * * *